United States Patent
Oshima et al.

(10) Patent No.: US 7,966,063 B2
(45) Date of Patent: Jun. 21, 2011

(54) BODY COMPOSITION MEASURING APPARATUS

(75) Inventors: Yoshitake Oshima, Kyoto (JP); Tetsuya Sato, Nishinomiya (JP); Toshikazu Shiga, Otsu (JP)

(73) Assignee: OMRON HEALTHCARE Co., Ltd., Kyoto-shi (JP)

( * ) Notice: Subject to any disclaimer, the term of this patent is extended or adjusted under 35 U.S.C. 154(b) by 1112 days.

(21) Appl. No.: 11/370,806

(22) Filed: Mar. 9, 2006

(65) Prior Publication Data

US 2006/0206271 A1   Sep. 14, 2006

(30) Foreign Application Priority Data

Mar. 11, 2005   (JP) .................................. 2005-069732

(51) Int. Cl.
*A61B 5/05* (2006.01)
(52) U.S. Cl. ......................................................... 600/547
(58) Field of Classification Search .................... 600/547
See application file for complete search history.

(56) References Cited

U.S. PATENT DOCUMENTS

| | | | |
|---|---|---|---|
| 6,256,532 B1 * | 7/2001 | Cha | 600/547 |
| 2004/0059242 A1 | 3/2004 | Masuo et al. | |
| 2005/0059902 A1 * | 3/2005 | Itagaki | 600/547 |

FOREIGN PATENT DOCUMENTS

| | | |
|---|---|---|
| EP | 1-514-513 A1 | 3/2005 |
| JP | 2000-139869 A | 5/2000 |
| JP | 2001-157672 | 6/2001 |
| JP | 2002-325741 | 11/2002 |
| JP | 2003-70762 | 3/2003 |
| JP | 2003220048 * | 8/2003 |
| JP | 2004-255015 | 9/2004 |
| WO | WO-02/43586 | 6/2002 |
| WO | WO-02/43586 A1 | 6/2002 |

OTHER PUBLICATIONS

Japanese Notice of Grounds of Rejection mailed Jan. 11, 2011, directed to counterpart Japanese Application No. 2005-069732; 5 pages.

* cited by examiner

*Primary Examiner* — Max Hindenburg
*Assistant Examiner* — Helen Q. Nguyen
(74) *Attorney, Agent, or Firm* — Morrison & Foerster LLP (57) ABSTRACT

There are provided a hold portion that can be held in a hand of a subject, a cable having one end connected to the hold portion, and a rest portion on which a foot of the subject can be rested. The rest portion includes a reel portion connected to the other end of the cable for winding the cable, a first detection unit for detecting a draw-out extent to which the cable is drawn out from the reel portion, and a second detection unit for detecting an angle formed by the rest portion and the cable. Based on the detected draw-out extent and angle, the part length of a body part of the subject is calculated.

14 Claims, 10 Drawing Sheets

BODY COMPOSITION MEASURING APPARATUS

BACKGROUND OF THE INVENTION

1. Field of the Invention

The present invention relates to a body composition measuring apparatus, and particularly to a body composition measuring apparatus for measuring the body composition of each of body parts.

2. Description of the Background Art

There has conventionally been an apparatus for measuring the body composition based on the bioelectrical impedance method. In recent years, various apparatuses have been proposed with which the body composition, for example, body fat percentage can easily be measured accurately even at home.

As an example, Japanese Patent Laying-Open No. 2001-157672 discloses a small-sized and light-weight healthcare guideline advising device that can calculate the body fat percentage and fat free mass for example of a subject based on a value of measured impedance as well as such body-specifying information as the height, weight, age and gender of the subject. Thus, the body composition of the subject can be calculated even at home.

Further, International Publication No. WO2002/043586 discloses a body composition measuring apparatus that can calculate the body composition, for example, the muscle mass of each part of the subject's body. According to this document, based on a measurement of impedance corresponding to each body part as well as such body-specifying information as the height or the length of each body part, weight, age and gender of the subject, the body composition of each part of the subject is calculated. The document indicates that, in calculating the body composition of each body part, the length of each part can also be estimated by multiplying an input height by a certain factor. Accordingly, the body composition of each body part can be calculated.

The art of Japanese Patent Laying-Open No. 2001-157672 described above is required to measure and input, on a separate occasion, at least the height among items of the body-specifying information. Further, the art of International Publication No. WO2002/043586 is required to separately measure and input the height or the length of each body part among items of the body-specifying information. In particular, to separately measure and input the length of each body part is troublesome for the subject.

In addition, as for International Publication No. WO2002/043586, the length of each part of the subject may be estimated by multiplying the height of the subject by a certain factor. In this case, however, a standard person of an appropriate age and gender for example is used as a model and thus if the subject is particularly developed in specific body part, through everyday training or long-term custom for example, like an athlete, there could be a possibility of an increased error.

SUMMARY OF THE INVENTION

The present invention has been made for solving the problems as described above. An object of the invention is to provide a body composition measuring apparatus that can lessen the degree of complexity in input by a subject.

According to an aspect of the present invention, a body composition measuring apparatus includes: a plurality of electrodes to be in contact with a plurality of predetermined parts, associated respectively with the electrodes, of the body of a subject; a hold portion that can be held in hands of the subject; a cable having one end connected to the hold portion; and a rest portion on which feet of the subject can be rested. The rest portion includes: a reel portion connected to the other end of the cable for winding the cable; a first detection unit for detecting a draw-out extent to which the cable is drawn out from the reel portion; and a second detection unit for detecting an angle formed by the rest portion and the cable. The body composition measuring apparatus further includes a first part-length calculation unit for calculating the part length of a body part of the subject based on the draw-out extent detected by the first detection unit and the angle detected by the second detection unit; a first measurement unit for measuring impedance of the body part by using the plurality of electrodes; and a first body composition calculation unit for calculating body composition of the body part based on the calculated part length and the measured impedance.

Here, "part length" refers to the length in the axial direction of each body part.

Preferably, the body composition measuring apparatus further includes: an operation unit operated by the subject; and a sense unit for sensing an instruction signal from the operation unit. The first part-length calculation unit calculates the part length of the body part when the sense unit senses the instruction signal for instructing to start calculation of the part length.

Preferably, the plurality of electrodes include electrodes for hands provided to the hold portion and including at least a pair of an electrode for current and an electrode for voltage, and electrodes for feet provided to the rest portion and including at least a pair of the electrode for current and the electrode for voltage.

Alternatively, the plurality of electrodes preferably include electrodes for hands provided to the hold portion and including at least a pair of an electrode for current and an electrode for voltage.

Alternatively, the plurality of electrodes preferably include electrodes for feet provided to the rest portion and including at least a pair of an electrode for current and an electrode for voltage.

Preferably, the body part is arm portion. The first part-length calculation unit calculates the part length of the arm portion by using a predetermined expression based on the draw-out extent and the angle.

Preferably, the body composition measuring apparatus further includes: a second part-length calculation unit for calculating the part length of a leg portion of the subject based on the draw-out extent detected by the first detection unit; a second measurement unit for measuring the impedance of the leg portion by using the electrodes for feet and the electrodes for hands; and a second body composition calculation unit for calculating the body composition of the leg portion based on the calculated part length of the leg portion and the measured impedance of the leg portion.

Preferably, the body composition measuring apparatus further includes: an operation unit operated by the subject; and a sense unit for sensing an instruction signal from the operation unit. The second part-length calculation unit calculates the part length of the leg portion when the sense unit senses the instruction signal for instructing to start calculation of the part length.

Preferably, the body part is trunk. The first part-length calculation unit calculates the part length of the trunk by using a predetermined expression based on the draw-out extent, the angle and the part length of the leg portion.

Preferably, the body part includes arm portion and trunk. The body composition measuring apparatus further includes a third body composition calculation unit for calculating the body composition of the whole body of the subject based on the body composition of the arm portion and the trunk calculated by the first body composition calculation unit and the body composition of the leg portion calculated by the second body composition calculation unit.

Preferably, the body composition includes at least one of body fat mass, body fat percentage, fat free mass, fat free percentage, bone mineral density, muscle mass, and muscle percentage.

According to the present invention, the part length of a body part can be calculated and thus the subject is relieved of the trouble of measuring the part length in advance. Further, for the subject, it is unnecessary to input the part length of the subject's body part and thus the subject is relieved of troublesome manual input.

In addition, since the calculated part length of the body part is used, the body composition can precisely be measured.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

An embodiment of the present invention is now described in detail with reference to the drawings. In the drawings, like or corresponding elements are denoted by like reference characters and the description thereof is not repeated.

<Appearance and Structure of a Body Composition Measuring Apparatus in the Present Embodiment of the Invention>

Figure 1:
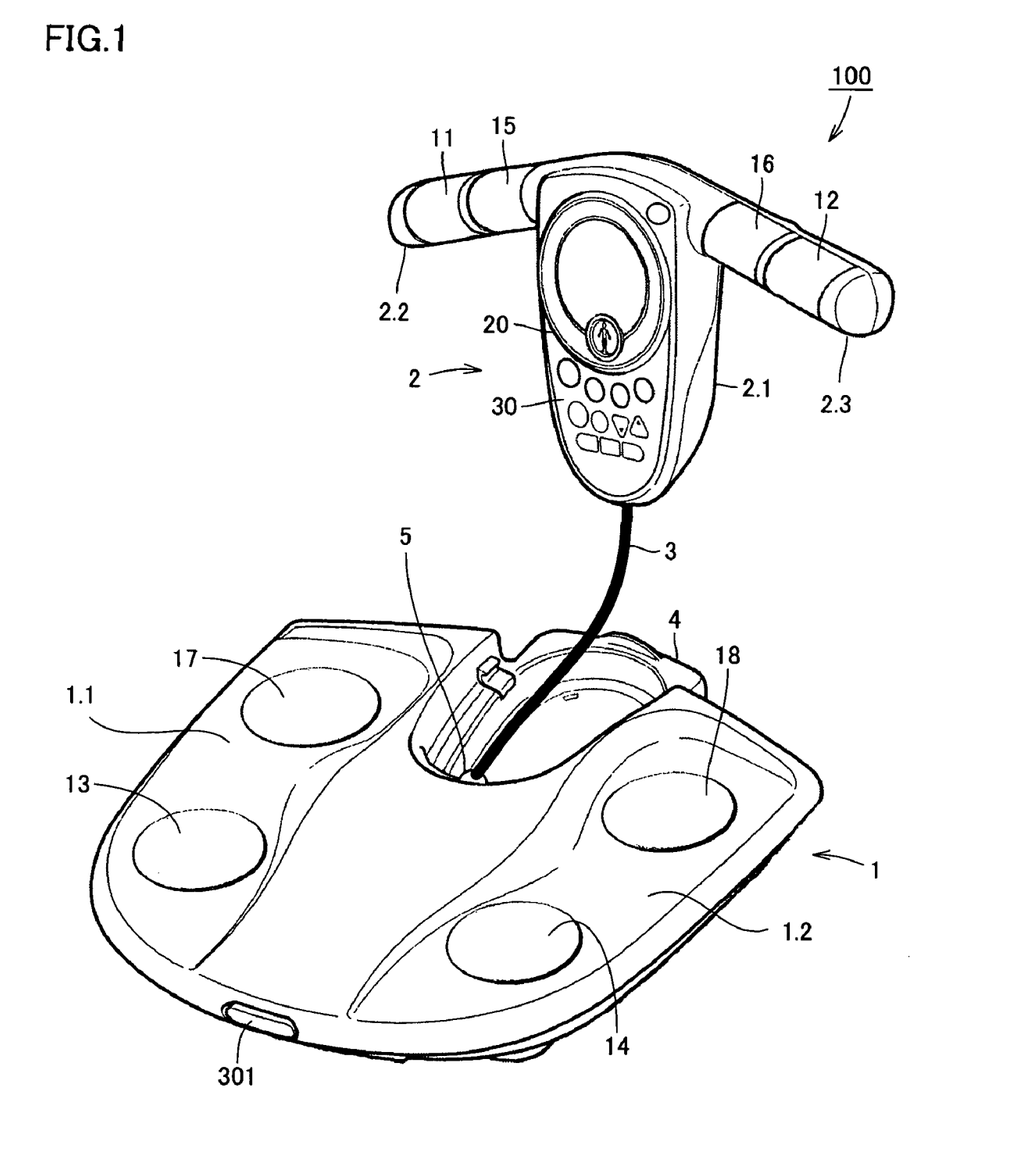
FIG. 1 is an external perspective view of a body composition analyzer in an embodiment of the present invention.

FIG. 1 is an external perspective view of a body composition measuring apparatus (hereinafter referred to as "body composition analyzer") 100 in the embodiment of the present invention.

Referring to FIG. 1, body composition analyzer 100 includes a rest portion 1 on which a foot of a subject can be rested, a hold portion 2 that can be held in a hand of the subject, and a cable 3 for electrically connecting rest portion 1 and hold portion 2. Body composition analyzer 100 is provided with a plurality of electrodes 11 to 18 to be in contact with a plurality of predetermined parts respectively, associated with respective electrodes, of the body of the subject.

Rest portion 1 is provided with a left-foot rest portion 1.1 on which the left foot of the subject is to be rested, a right-foot rest portion 1.2 on which the right foot of the subject is to be rested, and a receptacle 4 for receiving hold portion 2 and cable 3. Further, in the present embodiment, rest portion 1 is provided with a rotation shaft 5 connected to one end of cable 3 with its other end connected to hold portion 2, for reeling cable 3. Furthermore, a weight measurement unit 32 (see FIG. 3) for measuring the weight of the subject, weight sensor for example, is provided.

Left-foot rest portion 1.1 and right-foot rest portion 1.2 are each provided with two electrodes to be in contact with the sole of the subject. To left-foot rest portion 1.1, a current-application electrode 17 is provided in a region where the left toe is to be positioned while a voltage-measurement electrode 13 is provided in a region where the left heel is to be positioned. Likewise, to right-foot rest portion 1.2, a current-application electrode 18 is provided in a region where the right toe is to be positioned and a voltage-measurement electrode 14 is provided in a region where the right heel is to be positioned.

Moreover, left-foot rest portion 1.1 and right-foot rest portion 1.2 are each formed to substantially have the shape of the outline of the foot for allowing the right and left feet of the subject to contact the above-described electrodes 13, 14, 17, 18 when the subject puts both feet on the rest portions. Thus, even if both of the soles of the right and left feet are displaced from left-foot rest portion 1.1 and right-foot rest portion 1.2 in the lateral direction, it rarely occurs that the soles are displaced from current-application electrodes 17, 18 and voltage-measurement electrodes 13, 14. Therefore, an error can be prevented from occurring due to changes in contact part and contact area. In addition, influences of changes in the state of contact between the thighs can also be prevented. Accordingly, highly reliable measurement can be performed.

Hold portion 2 is comprised of a main portion 2.1, a left-hand grip portion 2.2 to be gripped in the subject's left hand and a right-hand grip portion 2.3 to be gripped in the subject's right hand.

On the front side of main portion 2.1, there are provided a display unit 20 for displaying the result of measurement and various information as well as an operation unit 30 operated by the subject for receiving instructions and inputs of various information from the subject. Regarding display unit 20 and operation unit 30 provided to main portion 2.1 of hold portion 2, a detailed description is hereinlater given with reference to FIG. 4.

In the present embodiment, a power switch 301 included in operation unit 30 is provided for example at the center of the front side of rest portion 1 for example.

Grip portions 2.2 and 2.3 of hold portion 2 are each provided with two electrodes to be in contact with the inner side of the subject's hand. Left-hand grip portion 2.2 is provided with a current-application electrode 15 placed on the side corresponding to the thumb of the left hand as well as a voltage-measurement electrode 11 placed on the side corresponding to the little finger of the left hand. Likewise, right-hand grip portion 2.3 is provided with a current-application electrode 16 placed on the side corresponding to the thumb of the right hand and a voltage-measurement electrode 12 placed on the side corresponding to the little finger of the right hand.

Thus, body composition analyzer 100 in the embodiment of the present invention is structured to allow current-application and voltage-measurement electrodes to be in contact with the four parts, namely left hand, right hand, left foot and right foot. The structure is not limited to the aforementioned one. For example, additional current-application and voltage-measurement electrodes may be provided for other parts. Alternatively, for example, a pair of a current-application electrode and a voltage-measurement electrode may be provided to one of left-foot rest portion 1.1 and right-foot rest portion 1.2. Similarly, a pair of a current-application electrode and a voltage-measurement electrode may be provided to one of left-hand grip portion 2.2 and right-hand grip portion 2.3.

Figure 2:
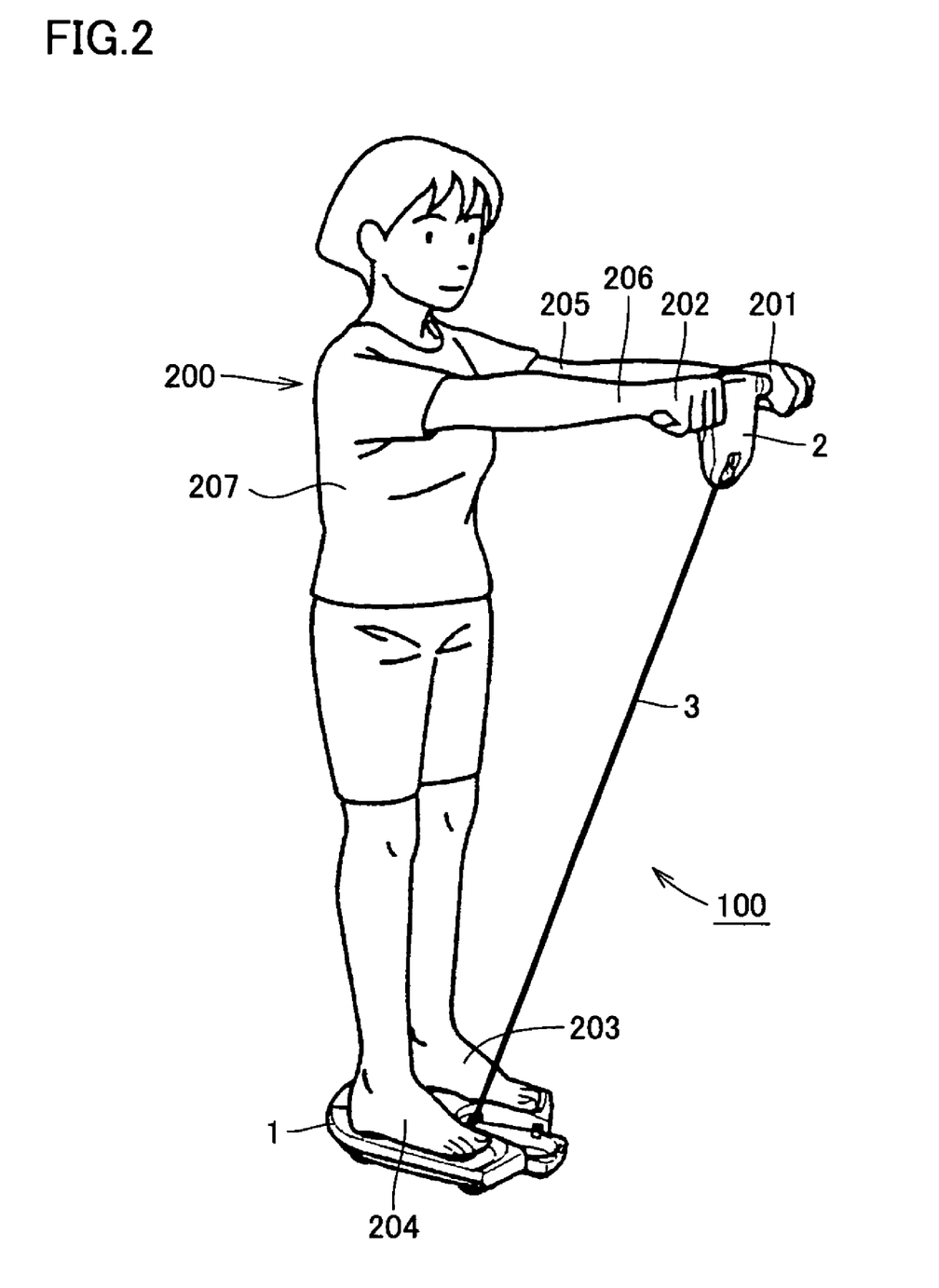
FIG. 2 shows a posture for measurement taken when a subject uses the body composition analyzer in the embodiment of the present invention to measure the body composition.

FIG. 2 shows a posture for measurement taken when a subject uses body composition analyzer 100 in the embodiment of the present invention to measure the composition of the body (hereinafter "body composition").

Referring to FIG. 2, subject 200 is in the upright posture with left foot 203 and right foot 204 positioned respectively on left-foot rest portion 1.1 and right-foot rest portion 1.2 of rest portion 1. Further, subject 200 holds grip portion 2.2 of hold portion 2 by left hand 201 while holding grip portion 2.3 by right hand 202. At this time, subject 200 extends respective elbows of both arms 205 and 206 and keeps the arms substantially at the level of shoulder to allow hold portion 2 to be opposite to the front of the body and thereby allow arms 205, 206 to be substantially orthogonal to trunk 207.

Figure 3:
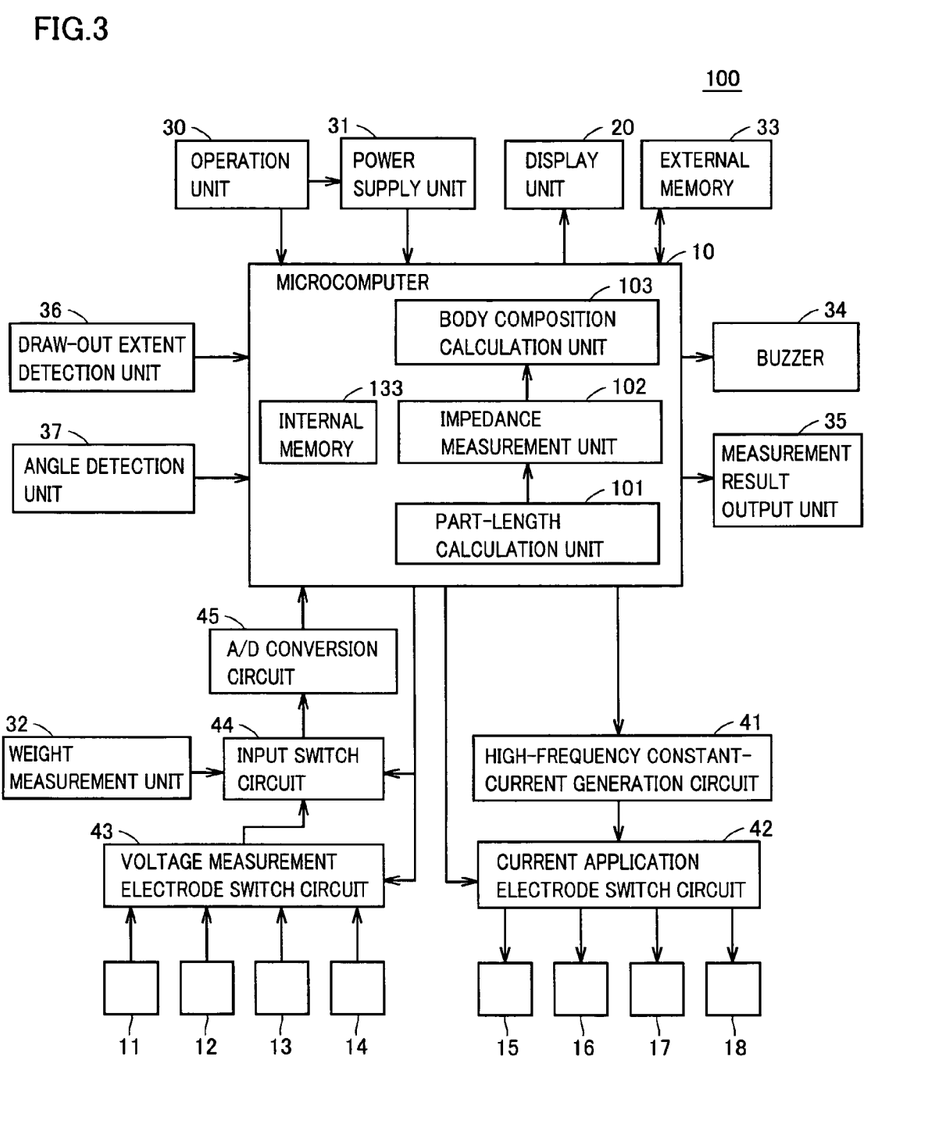
FIG. 3 is a block diagram of the body composition analyzer in the embodiment of the present invention.

FIG. 3 is a block diagram of body composition analyzer 100 in the embodiment of the present invention. Referring to FIG. 3, body composition analyzer 100 includes, in addition to a plurality of electrodes 11-18, display unit 20, operation unit 30 and weight measurement unit 32 described above, a microcomputer 10 for performing the overall control of body composition analyzer 100 and for performing various operations, a high-frequency constant-current generating circuit 41 for generating high-frequency constant-current at a predetermined frequency, a current application electrode switch circuit 42 for switching current-application electrodes 15-18, a voltage-measurement electrode switch circuit 43 for switching voltage-measurement electrodes 11-14, an input switch circuit 44 for switching an input to one of voltage information obtained from voltage-measurement electrode switch circuit 43 and weight information obtained from weight measurement unit 32, and an A (analog)/D (digital) conversion circuit 45 for converting the voltage information and weight information obtained from input switch circuit 44 from an analog signal into a digital signal. Body composition analyzer 100 includes a power supply unit 31 for supplying electric power to microcomputer 10 when power supply switch 301 included in operation unit 30 is operated, an external memory 33 for storing such information as measurement results, a buzzer 34 for generating an audible alarm, a measurement result output unit 35 for outputting the measurement result to a printer (not shown) by communication, a draw-out extent detection unit 36 for detecting a draw-out extent to which cable 3 is drawn out, and an angle detection unit 37 for detecting an angle formed by rest portion 1 and cable 3.

In the present embodiment, external memory 33 includes for example EEPROM (Electrically Erasable Programmable Read-Only Memory) and stores information about body parts of the subject as well as such measurement result as body composition.

In the embodiment of the present invention, "body part" refers to one of a plurality of body parts into which the whole body to be measured, namely the whole body except for the head portion, is divided. Therefore, the body part is one of the parts that are the torso and four limbs or one of parts into which the aforementioned parts are divided. In the present embodiment, body parts to be measured are arm portion, leg portion and trunk. "Arm portion" herein refers to at least one of the right and left arms, preferably both arms. "Leg portion" refers to at least one of the right and left legs, preferably both legs. In the following description, the arm portion is comprised of right and left arm portions and the leg portion is comprised of right and left leg portions.

"Left arm portion" and "right arm portion" each refer to the body part for example extending from the wrist to the acromion of the shoulder, "left leg portion" and "right leg portion" each refer to the body part for example extending from the heel to the top of the leg, and "trunk" refers to the body part representing the torso.

In the following description, the whole body and each body part to be measured is referred to as "measured part" or "part to be measured."

Referring again to FIG. 3, draw-out extent detection unit 36 is structured of a sensor, rotary encoder for example for detecting the number of rotations or angle of rotation of rotation shaft 5 mentioned above. Draw-out extent detection unit 36 includes, for example, a transducer for converting an output from the sensor into an electrical signal and an A/D converter for converting the analog signal that is output from the transducer into a digital signal. In the embodiment of the present invention, at least the sensor of draw-out extent detection unit 36 is provided to rest portion 1.

In the embodiment of the present invention, "draw-out extent of cable 3" refers to the length of the cable from rest portion 1 to the position near grip portions 2.2 and 2.3 in the state where cable 3 is strained. Therefore, draw-out extent detection unit 36 outputs, as the draw-out extent of cable 3, the sum of the actual length of cable 3 as drawn out and the magnitude corresponding to the longitudinal length of main portion 2.1. Draw-out extent detection unit 36 may detect the actual draw-out extent of cable 3. In this case, a part-length calculation unit 101, which is described hereinlater, may perform a calculation for correcting the draw-out extent.

Figure 7:
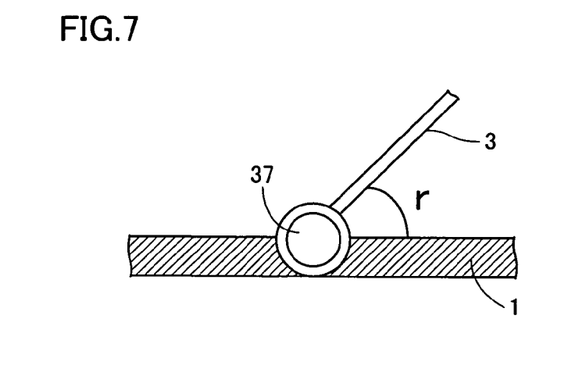
FIG. 7 is a schematic cross-sectional view showing an example of the way to mount an angle detection unit.

Angle detection unit 37 measures the rotation angle of cable 3 and outputs, for example, a change in resistance value in angle detection unit 37, as angle information. As shown in FIG. 7, angle detection unit 37 is provided to rest portion 1 for detecting angle r between rest portion 1 and cable 3.

Although draw-out extent detection unit 36 and angle detection unit 37 are provided to rest portion 1 according to the description above, they may be provided to hold portion 2.

Microcomputer 10 includes part-length calculation unit 101, an impedance measurement unit 102 and a body composition calculation unit 103, respectively for calculating the part length, measuring the impedance and calculating the body composition, according to a program stored in an internal memory 133. Further, based on a signal from weight measurement unit 32 that is obtained through A/D conversion circuit 45, microcomputer 10 measures the weight by a known method. Furthermore, microcomputer 10 generates a signal for displaying on display unit 20 the result of measurement for example by body composition calculation unit 103 described hereinlater. Moreover, writing and reading into and from external memory 33 is performed by microcomputer 10.

Part-length calculation unit 101 calculates the part length of a body part of a subject, based on signals from draw-out extent detection unit 36 and angle detection unit 37. In the embodiment of the present invention, part-length calculation unit 101 can calculate respective part lengths of all body parts of the subject. For example, the part length of the leg portion (right and left leg portions) is calculated based on the draw-out extent of cable 3 that is detected by draw-out extent detection unit 36. The part length of the arm portion (right and left arm portions) is calculated based on the draw-out extent of cable 3 detected by draw-out extent detection unit 36 and the angle detected by angle detection unit 37. The part length of the trunk is calculated based on the draw-out extent of cable 3 detected by draw-out extent detection unit 36, the angle detected by angle detection unit 37 and the part length of the leg portion.

More specifically, each part length can be determined in the following way.

Figure 5:
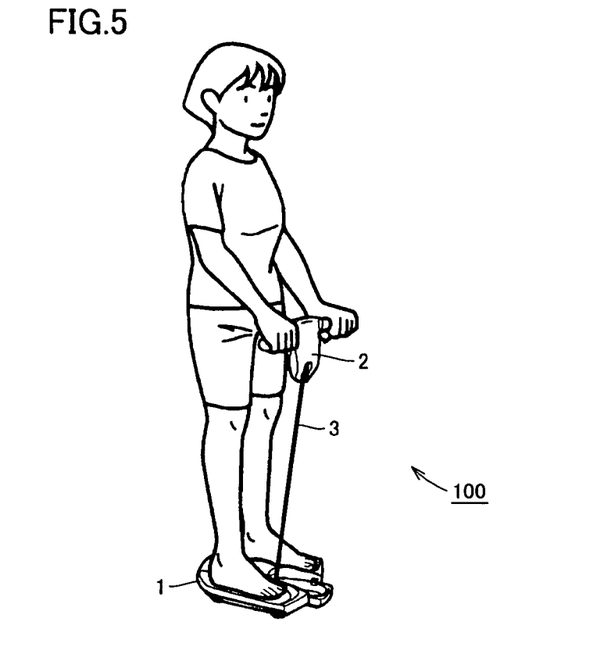
FIG. 5 illustrates how to calculate the part length of the leg portion.

First, a method of calculating the part length of the leg portion is described in connection with FIG. 5. As described in connection with FIG. 2, the subject undergoes the measurement in an upright posture while resting both feet on rest portion 1. Thus, as shown in FIG. 5, the top of the leg, namely the position of the groin may be matched with the position of grip portions 2.2 and 2.3 of hold portion 2 to determine the length of cable 3 as drawn out (draw-out extent) as the length of the leg, namely the part length of the leg portion.

Figure 6A:
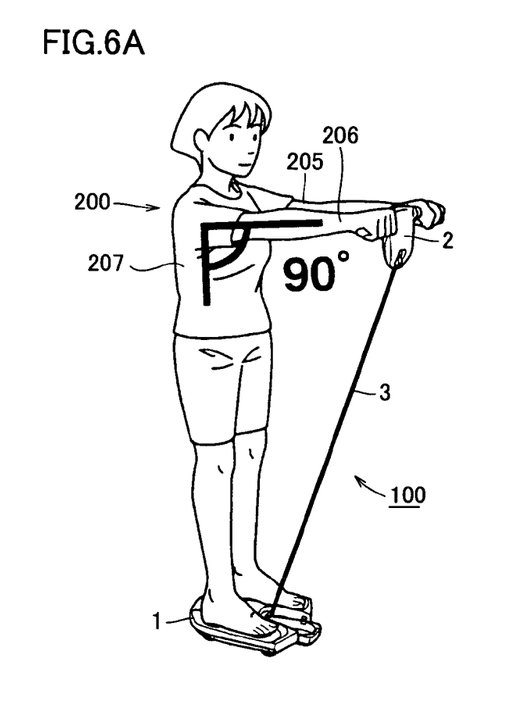
FIGS. 6A and 6B illustrate how to calculate the part length of the arm portion and trunk.
Figure 6B:
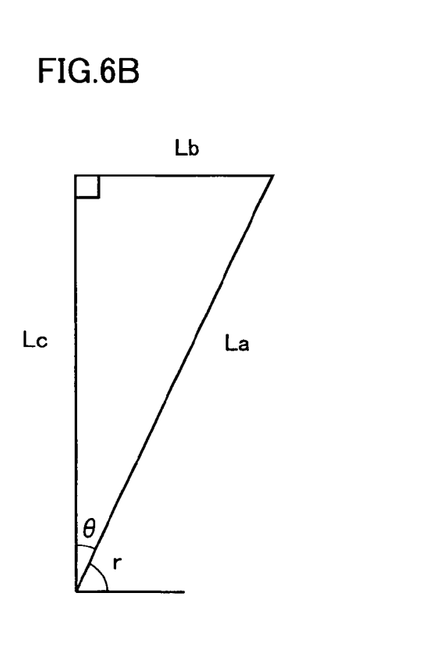

Next, a method of calculating the part length of the arm portion and the trunk is described in connection with FIGS. 6A and 6B. FIG. 6A shows a posture for measurement similar to the one in FIG. 2. Referring to FIG. 6A, when body composition analyzer 100 is used for measurement in the embodiment of the present invention, the posture is taken to allow both arms 205 and 206 and trunk 207 to substantially form a right angle. Thus, as seen from a lateral side, the posture for measurement of the subject can be regarded as a right-angled triangle having length La of cable 3 as the hypotenuse.

In the embodiment of the present invention, angle detection unit 37 detects angle r formed by rest portion 1 and cable 3. Thus, using the following expressions, part length Lb of the arm portion as well as the sum of the part length of the leg portion and the part length of the trunk, namely Lc can be determined.

$$\theta = 90 - r$$

$$Lc = La \times \cos\theta$$

$$Lb = La \times \sin\theta$$

Further, since the part length of the leg portion can be determined from the draw-out extent of cable 3 only, the part length of the trunk can be determined by subtracting the part length of the leg portion from length Lc.

Thus, by a predetermined operation before the subject takes the posture for measurement, the part length of the leg portion can be calculated. Subsequently, the subject takes the posture for measurement so as to allow respective part lengths of remaining body parts to be calculated.

It is supposed here that part-length calculation unit 101 starts to calculate the part length of each body part when a predetermined condition is satisfied. In the embodiment of the present invention, at the time that is after the start of measurement and that is the time when length determination switch 111 is first operated which is described hereinlater, the calculation of the part length of the leg portion is started.

Further, it is supposed that the calculation of respective part lengths of remaining body parts is started when length determination switch 311 is next operated. The operation by the subject may not be a trigger for starting the calculation. For example, display unit 20 or buzzer 34 may be used to inform the subject of the posture to be taken and the calculation may be started after a predetermined time has passed. Alternatively, the calculation may be started, by generating sound from buzzer 34, when a predetermined time has passed. Alternatively, the state of movement of hold portion 2 may be detected to start the calculation when it is determined that the hold portion 2 is stationary for a predetermined time.

Impedance measurement unit 102 measures the impedance of five body parts described above. Impedance measurement unit 102 controls current-application electrode switch circuit 42 and voltage-measurement electrode switch circuit 43, and successively selects necessary current-application electrodes and voltage-measurement electrodes to measure the impedance of each body part. More specifically, based on the value of current flown from high-frequency constant-current generation circuit 41 and a potential difference between two electrodes that is obtained through A/D conversion circuit 45, impedance measurement unit 102 measures the impedance of each body part.

Here, a method of measuring the impedance is specifically described.

Figure 8:
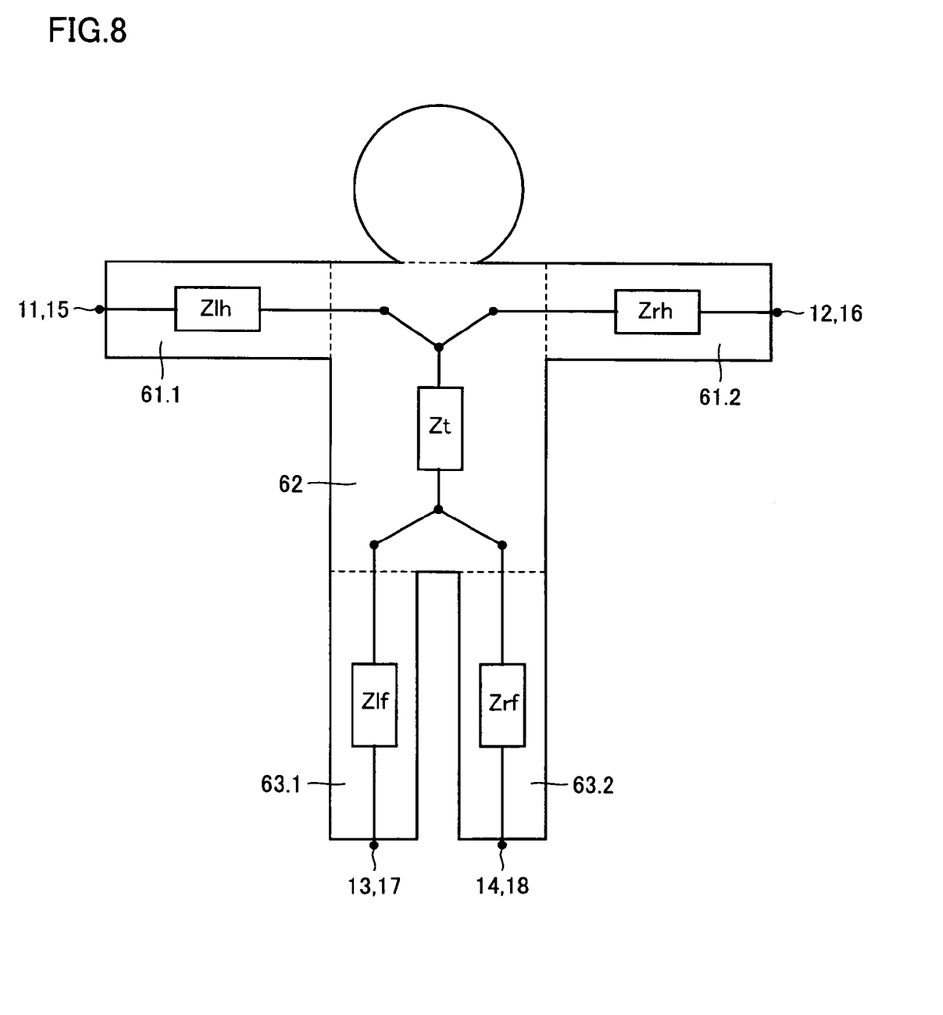
FIG. 8 schematically shows impedance of each body part.

FIG. 8 schematically shows impedance of each body part.

Referring to FIG. 8, the impedance of each body part is represented as follows. The impedance of left arm portion 61.1 is "Zlh," the impedance of right arm portion 61.2 is "Zrh," the impedance of left leg portion 63.1 is "Zlf," the impedance of right leg portion 63.2 is "Zrf" and the impedance of trunk 62 is "Zt."

Figure 9:
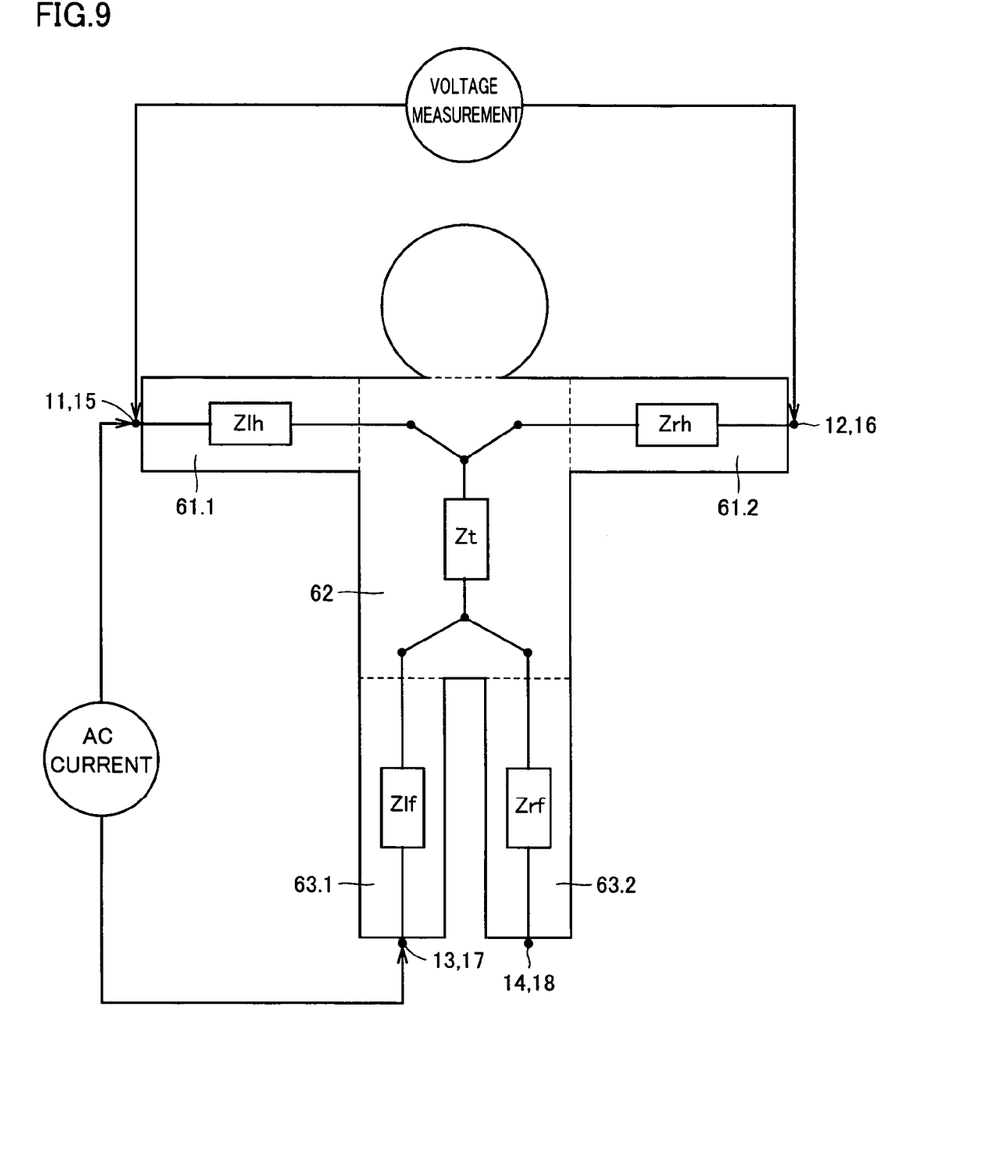
FIG. 9 illustrates how to measure impedance of a body part (left arm portion).

In the embodiment of the present invention, impedance measurement unit 102 measures the impedance of each body part. For example, impedance Zlh of left arm portion 61.1 is measured as shown in FIG. 9 by flowing AC current between the left hand and the left foot and measuring a potential difference between right and left hands. Specifically, impedance measurement unit 102 flows high-frequency (AC) current between current application electrodes 15 and 17 and measures the potential difference between voltage-measurement electrodes 11 and 12 to determine impedance Zlh of left arm portion 6.1.

Thus, impedance measurement unit 102 makes a switch between electrodes 11-18 to measure the impedance (Zlh, Zrh, Zt, Zlf, Zrf) of each body part.

Body composition calculation unit 103 calculates the body composition of each body part, based on the part length of each body part that is calculated by part-length calculation unit 101 and the impedance value of each body part that is measured by impedance measurement unit 102. Further, body composition calculation unit 103 calculates the body composition of the whole body based on respective body compositions of the five body parts into which the whole body is divided as described above.

In the present embodiment, "body composition of each body part" refers to at least the fat free mass of each body part and more preferably refers to such biological information as muscle mass, bone mineral density, body fat mass, in addition to the fat free mass. Further, "body composition of the whole body" refers to at least the fat free mass of the whole body and more preferably refers to the muscle mass, the bone mineral density, the body fat mass, body fat percentage, muscle percentage and visceral fat level, in addition to the fat free mass.

A method of calculating the body composition is specifically described.

The body composition of each body part is calculated as described below. For example, the fat free mass of each body part can be calculated with any expression like the one indicated below where the fat free mass is represented by FFM, the part length of each body part is represented by L, the weight is represented by W and predetermined factors are a to c.

$$FFM = a \cdot L^2/Z + b \cdot W + c$$

The expression is not limited this one and the expression may be the one taking into consideration the age and gender for example in addition to each part length and weight.

Further, using an expression similar to the expression for the fat free mass, muscle mass, body fat mass and bone mineral density for example of each body part can be calculated.

Further, in the embodiment of the present invention, the body composition of the whole body is calculated by using respective numerical values of the body composition of the body parts.

For example, fat free mass $FFM_A$ of the whole body can simply be calculated by using the following expression where the fat free mass of left arm portion 61.1 is $FFM_{0\_lh}$, the fat free mass of right arm portion 61.2 is $FFM_{0\_rh}$, the fat free mass of trunk 62 is $FFM_{0\_t}$, the fat free mass of left leg portion 63.1 is $FFM_{0\_lf}$, and the fat free mass of right leg portion 63.2 is $FFM_{0\_rf}$.

$$FFM_A = FFM_{0\_lh} + FFM_{0\_rh} + FFM_{0\_t} + FFM_{0\_lf} + FFM_{0\_rf}$$

The muscle mass of the whole body can also be calculated in a similar manner.

Moreover, from fat free mass $FFM_A$ of the whole body, the body fat mass of the whole body can be calculated. The body fat mass is represented by the following expression.

body fat mass (kg) = weight $W$ (kg) – fat free mass $FFM_A$ (kg)

Further, from the body fat mass of the whole body, the body fat percentage of the whole body can be calculated. The body fat percentage is represented by the following expression.

body fat percentage (%) = {body fat mass (kg) ÷ weight $W$ (kg)} × 100

Figure 4:
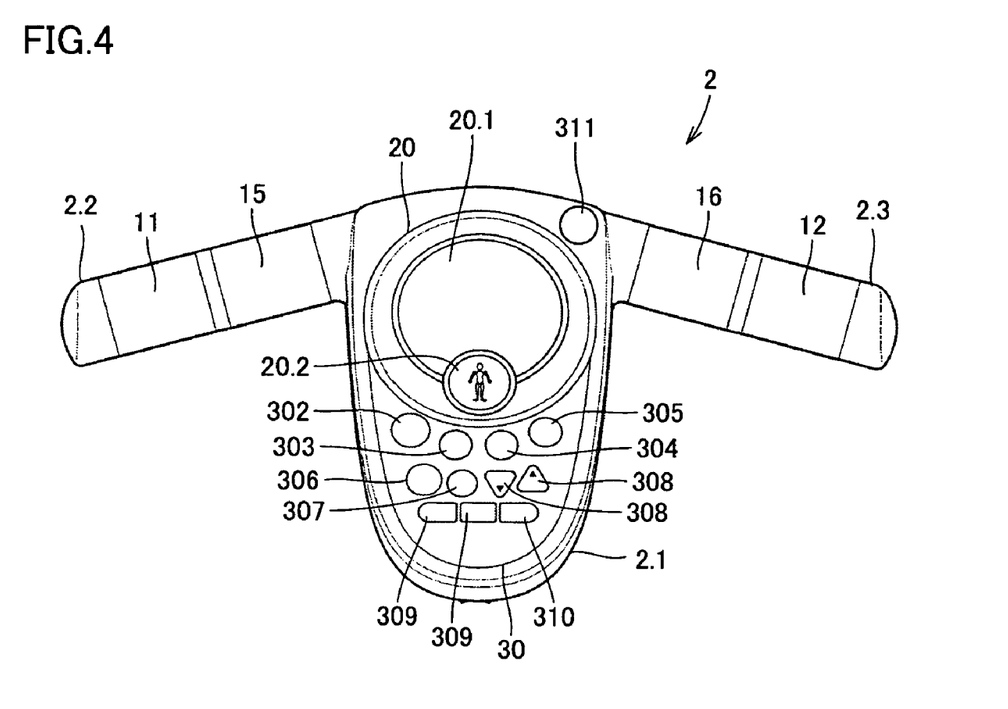
FIG. 4 is a front view of a hold portion.

A specific example of display unit 20 and operation unit 30 of body composition analyzer 100 in the embodiment of the present invention is shown in FIG. 4. FIG. 4 is a front view of hold portion 2.

Referring to FIG. 4, display unit 20 of main portion 2.1 of hold portion 2 includes a first display region 20.1 and a second display region 20.2. The first display region 20.1 and the second display region 20.2 are made for example of liquid crystal.

On the first display region 20.1, numerical values, characters and graphics for example representing the result of measurement for example are displayed. On the second display region 20.2, a figure of a body divided into a plurality of body parts (hereinafter referred to as "human body figure") is displayed. In the case where the result of measurement is displayed on the first display region 20.1, a portion of the human body figure corresponding to a measured part for which the result of measurement is displayed is illuminated. Accordingly, the subject can know information on the measured body part displayed on the first display region 20.1.

Display unit 20 is not limited to the above-described structure and may be any that can inform the subject of information about the measured body part as displayed.

Operation unit 30 is operated by the subject for example and includes a plurality of operation switches for receiving inputs of various information and instructions. For example, operation unit 30 includes a whole-body switch 302 for displaying such measurement result as the body composition of the whole body, a trunk switch 303 for displaying such measurement result as the body composition of the trunk, a leg switch 304 for displaying such measurement result as the body composition of the leg portion, an arm switch 305 for displaying such measurement result as the body composition of the arm portion, a setting/display switch 306 for setting and switching the display, a memory switch 307 for displaying the measurement result stored in external memory 33, an up/down switch 308 for increasing/decreasing a numerical value in making various settings, a personal number switch 309 for specifying information about the subject, a guest switch 310, and a length determination switch 311 for instructing to start calculation of the part length.

Whole-body switch 302, trunk switch 303, leg switch 304, and arm switch 305 are referred to collectively as "part-by-part switch."

In the present embodiment, when leg switch 304 is operated, a numerical value determined by combining the body composition of the left leg portion and the body composition of the right leg portion may be displayed or respective numerical values of the body composition of the right and leg portions may separately be displayed. Similarly, when arm switch 305 is operated, a numerical value determined by combining the body composition of the left arm portion and the body composition of the right arm portion may be displayed or respective numerical values of the body composition of respective right and left arms may separately be displayed.

Preferably, at least one personal number switch 309 is provided. In FIG. 4, two personal number switches are provided. In the present embodiment, for each of the numbers (1, 2) specified by personal number switches 309, information about and the measurement result for example of each body part of the subject are stored in external memory 33.

Guest switch 310 is pressed in the case for example where a subject other than subjects specified by personal number switches 309 is to undergo the measurement. Therefore, in the case where this switch is pressed at the start of measurement, the measurement process may be completed without storing the measurement results for example in external memory 33.

Length determination switch 311 is preferably placed at the position to allow the subject to operate the switch, above display unit 20 of main portion 2.1, for example, while holding grip portions 2.2 and 2.3. In FIG. 4, for example, length determination switch 311 is placed on the surface of main portion 2.1 and in the vicinity of the root portion of grip 2.3. Thus, the subject can operate the switch by the thumb of the right hand for example while holding grip portion 2.3.

Operation unit 30 may not be comprised of operation switches as described above. For example, the operation unit may be a touch panel for example with which various information and instructions are input.

<Operation of the Body Composition Analyzer in the Embodiment of the Invention>

Figure 10:
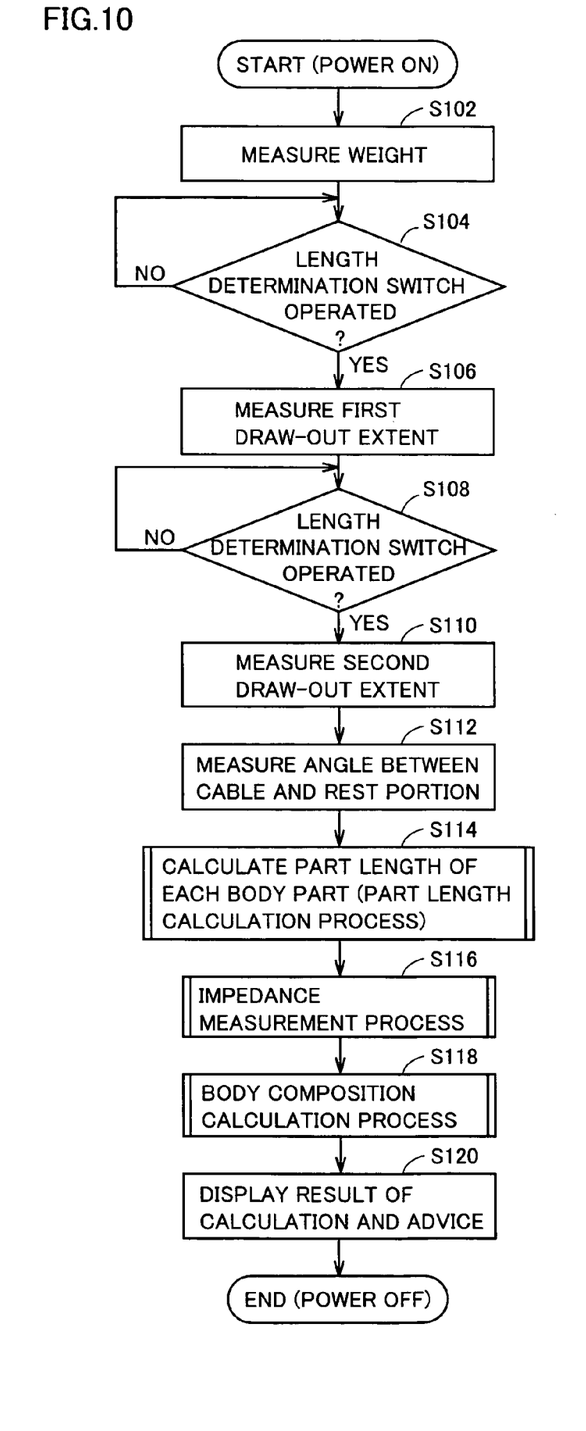
FIG. 10 is a flowchart showing a flow of a measurement process carried out by a microcomputer of the body composition analyzer in the embodiment of the present invention.

FIG. 10 is a flowchart showing a flow of a measurement process executed by microcomputer 10 of body composition analyzer 100 in the embodiment of the present invention. The measurement process is a process started upon operation of power switch 301 to cause electric power to be supplied from power supply unit 31 to microcomputer 10. Further, the process indicated below is described, supposing that one of personal number switch 309 and guest switch 310 is pressed.

First, microcomputer 10 measures the weight based on a signal from weight measurement unit 32 (step S102). The numerical value of the weight measured here is temporarily stored in a predetermined region of internal memory 133.

Next, microcomputer 10 determines whether or not length determination switch 311 is operated (step S104). Microcomputer 10 waits until it detects that length determination switch 311 is operated (NO in step S104). In this case, preferably the subject is informed of the timing at which length determination switch 311 should be operated. For example, such a message as "please match the position of your hands with the region near the groin while gripping hold portion 2 and, if match, please press length determination switch 311" is indicated on display unit 20. Accordingly, it can be prevented that the subject operates length determination switch 311 while the position is in error. Accordingly, the part length of the body part (leg portion) can accurately be calculated.

In step S104, if it cannot be detected, when a predetermined time has passed, that length determination switch 311 is operated, this measurement process may be ended.

When operation of length determination switch 311 is detected (YES in step S104), part-length calculation unit 101 of microcomputer 10 measures a first draw-out extent based on a signal from draw-out extent detection unit 36 (step S106). The first draw-out extent measured here is temporarily stored for example in a predetermined region of internal memory 133.

When the operation in step S106 is completed, microcomputer 10 again determines whether or not length determination switch 311 is operated (step S108). Microcomputer 10 waits until it detects that length determination switch 311 is operated (NO in step S108). Here, as well, it is preferable that the subject is informed of the timing at which length determination switch 311 should be operated. For example, such a message as "please take the posture for measurement while gripping hold portion 2 and, if take, please press length determination switch 311" is displayed on display unit 20. Accordingly, it can be prevented that the subject operates length determination switch 311 while the position is in error. Thus, the part lengths of the body parts (arm portion and trunk) can accurately be calculated.

When it is detected that length determination switch 311 is operated (YES in step S108), part-length calculation unit 101 of microcomputer 10 measures a second draw-out extent (step S110). The draw-out extent measured here is temporarily stored for example in a predetermined region of internal memory 133.

Subsequently, based on a signal from angle detection unit 37, part-length calculation unit 101 of microcomputer 10 measures angle r formed by cable 3 and rest portion 1 (step S112). Angle r measured here is temporarily stored for example in a predetermined region of internal memory 133.

Then, part-length calculation unit 101 calculates the part length of each body part based on measurements taken in steps S106, S110 and S112 (step S114). A subroutine of the part-length calculation process in step S114 is shown in FIG. 11.

Figure 11:
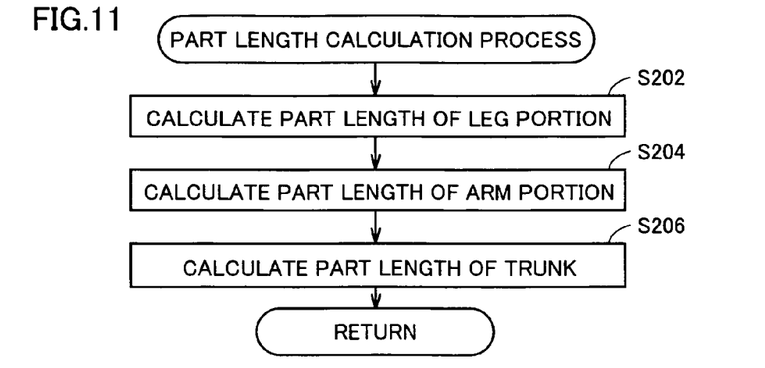
FIG. 11 is a flowchart showing a flow of a part-length calculation process in the embodiment of the present invention.

Referring to FIG. 11, based on the first draw-out extent measured in step S106, the part length of the leg portion is calculated (step S202). Further, based on the second draw-out extent measured in step S110 and the angle measured in step S112, the part length of the arm portion is calculated (step S204). Furthermore, based on the second draw-out extent measured in step S110, the angle measured in step S112 and the part length of the leg portion, the part length of the trunk is calculated (step S206). The process in step S202 and that in step S204 may be carried out in the reverse order. Since the specific method of calculating each part length is the one as described above, the description is not repeated here.

Following this, impedance measurement unit 102 of microcomputer 10 measures the impedance of each body part (step S116). A subroutine of the impedance measurement process in step S116 is shown in FIG. 12.

Figure 12:
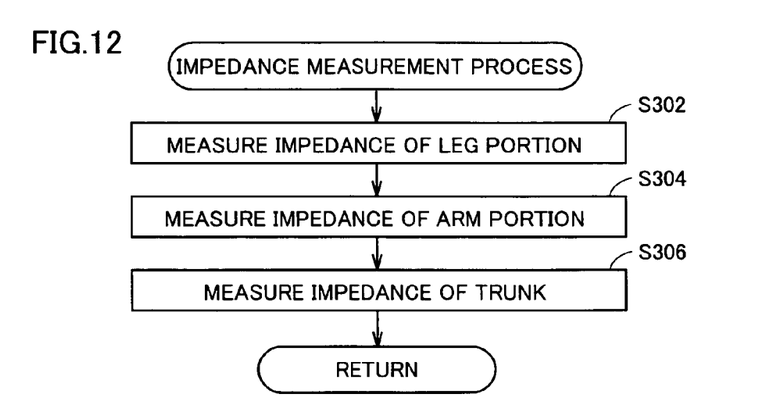
FIG. 12 is a flowchart showing a flow of an impedance measurement process in the embodiment of the present invention.

Referring to FIG. 12, the impedance of the leg portion is first measured (step S302). Then, respective impedances of the arm portion and the trunk are measured (steps S304, 306). The order in which the measurements of impedance are taken is not limited to the above-described one and may be taken in parallel for example. Further, since the specific method of measuring the impedance of each body part is the one as described above, the description is not repeated here.

Based on the part length of each body part calculated in step S114 and the value of impedance of each body part measured in step S116, the body composition of the whole body and that of each body part of the subject are calculated (step S1118). A subroutine of the body composition calculation process in step S118 is shown in FIG. 13.

Figure 13:
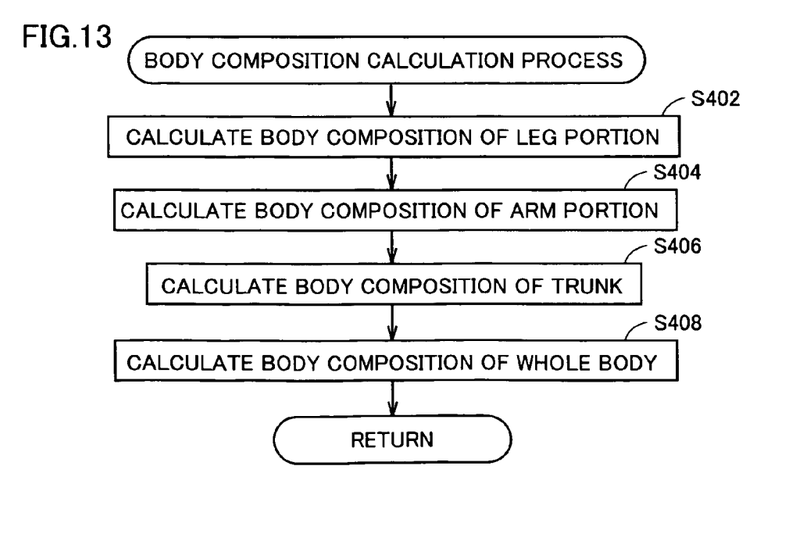
FIG. 13 is a flowchart showing a flow of a body composition calculation process in the embodiment of the present invention.

Referring to FIG. 13, the body composition of the leg portion is first calculated (step S402). Then, respective body compositions of the arm portion and the trunk are calculated (steps S404, 406). Based on respective body compositions of the body parts calculated in steps S402-S406, the body composition of the whole body is calculated (step S408). The order of steps S402-S406 is not limited to the above-described order and they may be carried out in parallel for example. The specific method of calculating the body composition of each part and the whole body is the one as described above, and the description is not repeated here.

While the part-length calculation process (step S114), the impedance measurement process (step S116) and the body composition calculation process (step S118) are successively carried out in the present embodiment, they may be performed in parallel.

The result of measurement in step S118 is displayed on display portion 20 together with resultant advice (step S120). Thus, the measurement process in the embodiment of the present invention is ended.

Figure 14A:
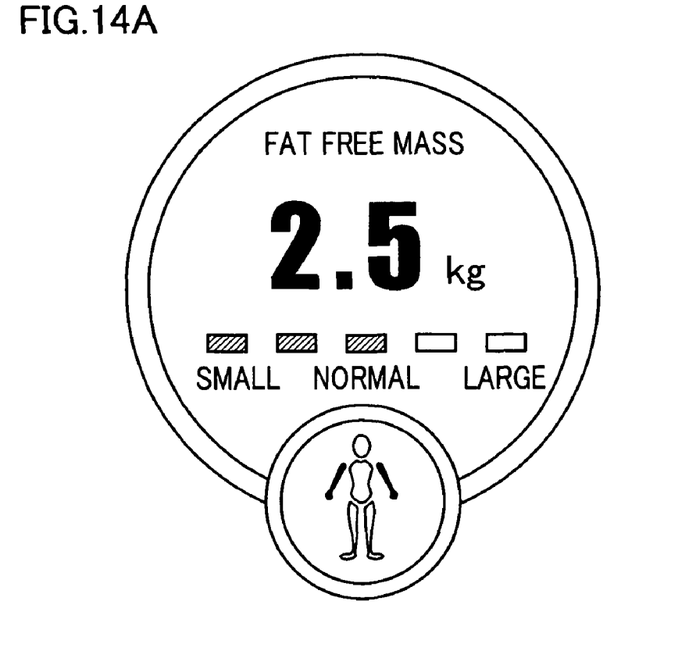
FIGS. 14A and 14B show respective examples of the way to display the measurement results of the arm portion and leg portion.
Figure 14B:
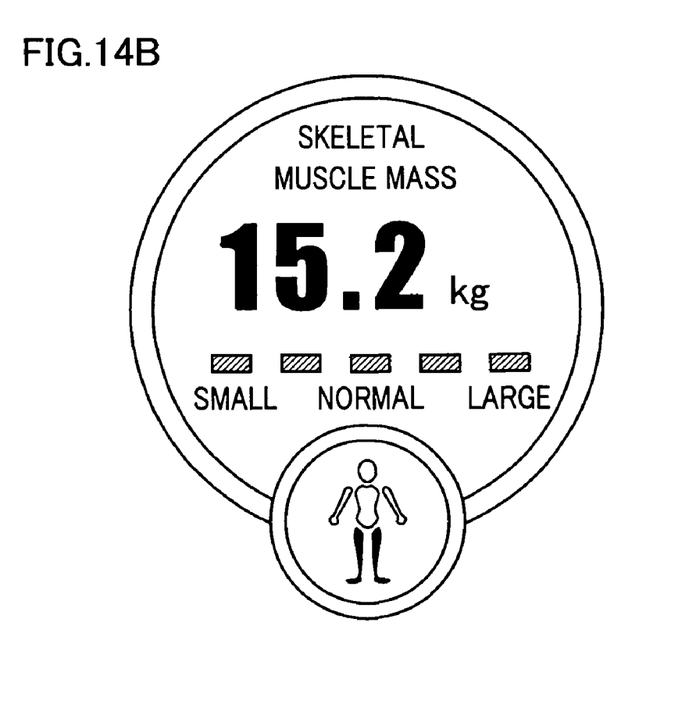

An example of display in step S120 is shown in FIGS. 14A and 14B.

FIG. 14A shows an example of display of fat free mass in the case where arm switch 305, which is one of part-by-part switches 302-305, is pressed for example. Referring to FIG. 14A, on the first display region 20.1, the fat free mass "2.5 kg" of the arm portion is displayed and the resultant advice "normal" is also displayed. Further, on the second display region 20.2, the arm portion in the human body figure is illuminated. As the resultant advice, information is displayed about whether or not the numerical value of the body composition being displayed is large or small as compared with a standard value stored in advance, for example.

FIG. 14B shows an example of display of the muscle mass in the case where leg switch 304 for example is pressed. Referring to FIG. 14B, on the first display region 20.1, the skeletal muscle mass (muscle mass) "15.2 kg" of the leg portion is displayed and the resultant advice "large" is also displayed. Further, on the second display region 20.2, the leg portion in the human body figure is illuminated.

In a similar manner, when other part-by-part switches 302, 303 are pressed, respective measurement results of the measured parts are displayed. Therefore, from a comparison between respective body compositions of body parts, the subject can know the balance of the degree to which muscle is developed in respective parts, for example.

The part length of each body part calculated in step S114 described above may be displayed on display unit 20. Thus, the subject can know the length of the leg and the length of the arm.

Further, in the case where personal number switch 309 is pressed immediately after the start of the above-described measurement process, the resultant measurement correlated with the personal number is stored in external memory 33. Thus, the subject can know any change in body composition of each measured part.

As discussed above, in the embodiment of the present invention, the subject is relieved of the trouble of measuring the part length of each body part, and thus the body composition can easily be measured at home for example. Accordingly, the troublesomeness of the subject can be removed. Further, since the part length of each body part can be used to calculate the body composition of each body part, a reliable numerical value of the body composition can be provided to the subject.

Furthermore, as discussed above, since each body part length and weight that are necessary for calculation of the body composition (fat free mass for example) of each body part are automatically measured, no manual input is necessary. Accordingly, availability for people in a wide range of ages can be achieved.

Moreover, electrically connected cable 3 can be used as a measure tape of a digital measure and thus is excellent in handling. If rest portion 1 and hold portion 2 communicate with each other in wireless manner, a measure tape may separately be provided instead of cable 3.

According to the description above, the body composition of the whole body is calculated based on respective body compositions of all body parts. However, the composition of the whole body may be calculated from the body height and the impedance of the whole body. In this case, cable 3 may be drawn strait to a position above the head, and the height can also be measured.

In addition, steps S104 and S106 in FIG. 10 may not be performed. In this case, only the part length of the leg portion may be manually input and the posture for measurement may be taken so as to calculate the part length of the arm portion and that of the trunk.

Further, only in the case where the body composition is measured for the first time, each part length may be measured. In this case, each part length as measured is stored in external memory 33 in association with the number of the pressed personal number switch 309. Thus, the body composition can more easily be measured for the second and subsequent times.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A body composition measuring apparatus comprising:
   a plurality of electrodes to be in contact with a plurality of predetermined parts, associated respectively with said electrodes, of the body of a subject;
   a hold portion that can be held in a hand of said subject, the hold portion comprising a display unit to display body composition data;
   a cable having one end connected to said hold portion;
   a rest portion on which a foot of said subject can be rested, said rest portion comprising,
   a receptacle for receiving the hold portion, such that when the hold portion is received in the receptacle the hold portion is substantially encased in the rest portion,
   a reel portion connected to the other end of said cable for winding said cable,
   a first detection unit for detecting a draw-out extent to which said cable is drawn out from said reel portion, and
   a second detection unit for detecting an angle formed by said rest portion and said cable proximate to a top surface of the rest portion;
   said body composition measuring apparatus further comprising
   a first part-length calculation unit for calculating the part length of a body part of said subject based on said draw-out extent detected by said first detection unit and said angle detected by said second detection unit;
   a first measurement unit for measuring impedance of said body part by using said plurality of electrodes; and
   a first body composition calculation unit for calculating body composition of said body part based on said calculated part length and said measured impedance.

2. The body composition measuring apparatus according to claim 1, further comprising:
   an operation unit operated by the subject; and
   a sense unit for sensing an instruction signal from said operation unit, wherein
   said first part-length calculation unit calculates said part length of the body part when said sense unit senses the instruction signal for instructing to start calculation of the part length.

3. The body composition measuring apparatus according to claim 1, wherein
   said plurality of electrodes include
   electrodes for hand provided to said hold portion and including at least a pair of an electrode for current and an electrode for voltage, and
   electrodes for foot provided to said rest portion and including at least a pair of said electrode for current and said electrode for voltage.

4. The body composition measuring apparatus according to claim 3, wherein
   said body part is arm portion, and
   said first part-length calculation unit calculates the part length of said arm portion by using a predetermined expression based on said draw-out extent and said angle.

5. The body composition measuring apparatus according to claim 3, further comprising:
   a second part-length calculation unit for calculating the part length of a leg portion of said subject based on said draw-out extent detected by said first detection unit;
   a second measurement unit for measuring the impedance of said leg portion by using said electrodes for foot and said electrodes for hand; and
   a second body composition calculation unit for calculating the body composition of said leg portion based on said calculated part length of the leg portion and said measured impedance of the leg portion.

6. The body composition measuring apparatus according to claim 5, further comprising:
   an operation unit operated by the subject; and
   a sense unit for sensing an instruction signal from said operation unit, wherein
   said second part-length calculation unit calculates said part length of the leg portion when said sense unit senses the instruction signal for instructing to start calculation of the part length.

7. The body composition measuring apparatus according to claim 5, wherein
said body part is trunk, and
said first part-length calculation unit calculates the part length of said trunk by using a predetermined expression based on said draw-out extent, said angle and said part length of the leg portion.

8. The body composition measuring apparatus according to claim 5, wherein
said body part includes arm portion and trunk, and
said body composition measuring apparatus further comprises a third body composition calculation unit for calculating the body composition of the whole body of said subject based on said body composition of the arm portion and said body composition of the trunk calculated by said first body composition calculation unit and said body composition of the leg portion calculated by said second body composition calculation unit.

9. The body composition measuring apparatus according to claim 1, wherein
said plurality of electrodes include electrodes for hand provided to said hold position and including at least a pair of an electrode for current and an electrode for voltage.

10. The body composition measuring apparatus according to claim 9, wherein
said body part is arm portion, and
said first part-length calculation unit calculates the part length of said arm portion by using a predetermined expression based on said draw-out extent and said angle.

11. The body composition measuring apparatus according to claim 1, wherein
said plurality of electrodes include electrodes for foot provided to said rest portion and including at least a pair of an electrode for current and an electrode for voltage.

12. The body composition measuring apparatus according to claim 11, wherein
said body part is arm portion, and
said first part-length calculation unit calculates the part length of said arm portion by using a predetermined expression based on said draw-out extent and said angle.

13. The body composition measuring apparatus according to claim 1, wherein
said body composition includes at least one of body fat mass, body fat percentage, fat free mass, fat free percentage, bone mineral density, muscle mass, and muscle percentage.

14. A body composition measuring apparatus comprising:
a plurality of electrodes to be in contact with a plurality of predetermined parts, associated respectively with said electrodes, of the body of a subject;
a hold portion having a first portion to be held by a first hand of the subject and a second portion to be held by the second hand of the subject;
a cable having one end connected to said hold portion;
a rest portion having a first portion on which a first foot of the subject is to be placed and a second portion on which a second foot of the subject is to be placed,
said rest portion including
a reel portion connected to the other end of said cable for winding said cable,
a first detection unit for detecting a draw-out extent to which said cable is drawn out from said reel portion, and
a second detection unit for detecting an angle formed by said rest portion and said cable at a position substantially between the first and second portions of the rest portion;
said body composition measuring apparatus further comprising
a first part-length calculation unit for calculating the part length of a body part of said subject based on said draw-out extent detected by said first detection unit and said angle detected by said second detection unit;
a first measurement unit for measuring impedance of said body part by using said plurality of electrodes; and
a first body composition calculation unit for calculating body composition of said body part based on said calculated part length and said measured impedance,
wherein said plurality of electrodes comprises,
a plurality of hand electrodes positioned on the first portion of the hold portion,
a plurality of hand electrodes positioned on the second portion of the hold portion,
a plurality of foot electrodes positioned on the first portion of the rest portion, and
a plurality of foot electrodes positioned on the second portion of the rest portion,
wherein the portion of the cable connected to the hold portion is positioned between the first and second portions of the hold portion, and
wherein the reel portion is positioned between the first and second portions of the rest portion.

* * * * *